US006799970B2

United States Patent
Martin et al.

(10) Patent No.: US 6,799,970 B2
(45) Date of Patent: Oct. 5, 2004

(54) DENTAL IMPLANT

(76) Inventors: Jean-Paul Martin, Promenade Corniche Kennedy, 159, Marseille (FR), 13007; Jean Heraud, Avenue du Marechal Lyautay, 7, Marseille (FR), 13007

( * ) Notice: Subject to any disclaimer, the term of this patent is extended or adjusted under 35 U.S.C. 154(b) by 0 days.

(21) Appl. No.: 09/972,768

(22) Filed: Oct. 5, 2001

(65) Prior Publication Data

US 2002/0177102 A1 Nov. 28, 2002

(30) Foreign Application Priority Data

Oct. 9, 2000 (EP) .............................. 00203516

(51) Int. Cl.[7] .............................................. A61C 8/00
(52) U.S. Cl. ...................... 433/173; 623/16; 600/566; 606/170
(58) Field of Search ................. 433/172, 173, 433/174, 175, 176, 201.1; 623/16; 600/566, 567; 606/170, 171

(56) References Cited

U.S. PATENT DOCUMENTS

| | | | |
|---|---|---|---|
| 3,981,079 A | * | 9/1976 | Lenczycki .................. 433/174 |
| 4,244,689 A | * | 1/1981 | Ashman ..................... 433/175 |
| 4,480,997 A | | 11/1984 | Deutsch et al. ............. 433/221 |
| 4,490,116 A | | 12/1984 | Deutsch et al. ............. 433/221 |
| RE31,948 E | | 7/1985 | Deutsch et al. ............. 433/221 |
| 4,820,306 A | * | 4/1989 | Gorman et al. ............... 623/16 |
| 4,973,168 A | * | 11/1990 | Chan ......................... 366/139 |
| 5,205,746 A | * | 4/1993 | Chanavaz ................... 433/174 |
| 5,501,706 A | * | 3/1996 | Arenberg ..................... 623/16 |
| 5,542,847 A | * | 8/1996 | Margulies ................... 433/173 |
| 5,632,746 A | * | 5/1997 | Middleman et al. .......... 606/78 |
| 6,312,258 B1 | * | 11/2001 | Ashman ..................... 433/172 |
| 6,413,089 B1 | * | 7/2002 | Ashman et al. ............. 433/174 |

FOREIGN PATENT DOCUMENTS

| | | |
|---|---|---|
| EP | 0336082 A2 | 11/1989 |
| JP | 02063453 A * | 3/1990 |

* cited by examiner

Primary Examiner—John J. Wilson
(74) Attorney, Agent, or Firm—Townsend and Townsend and Crew LLP; Gerald T. Gray

(57) ABSTRACT

A dental implant for anchoring in a bone structure, comprising a head intended to support a dental prosthesis and a threaded root of cylindrical substance, in which the threaded root has an internal cavity and a lateral orifice through which this internal cavity opens out on the external lateral face of the root. The axial position of this orifice is such that when the implant is in position, this orifice opens out on a medullary zone of the bone structure

7 Claims, 2 Drawing Sheets

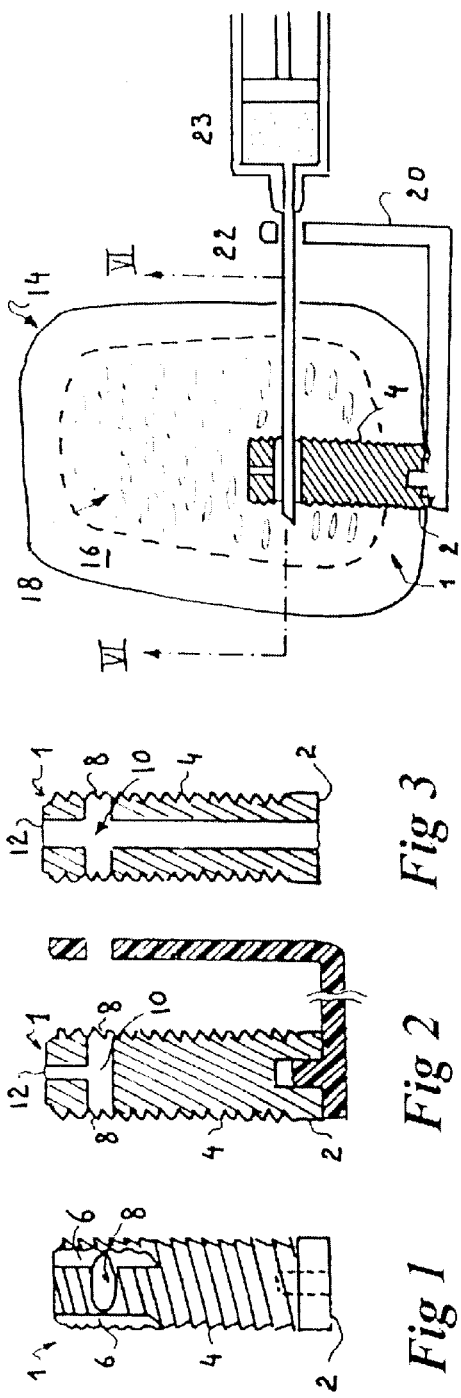

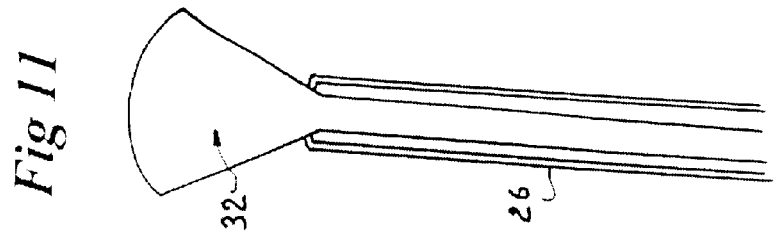
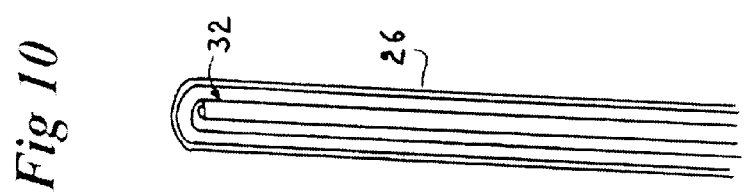
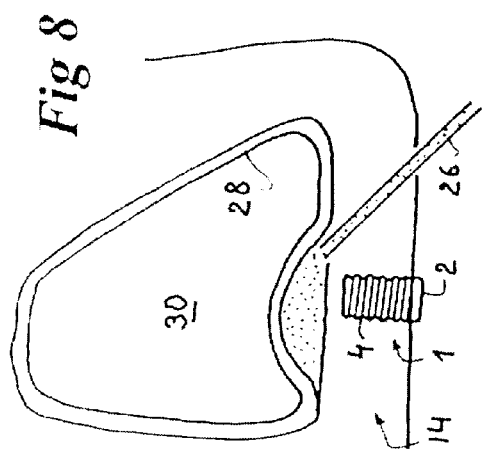
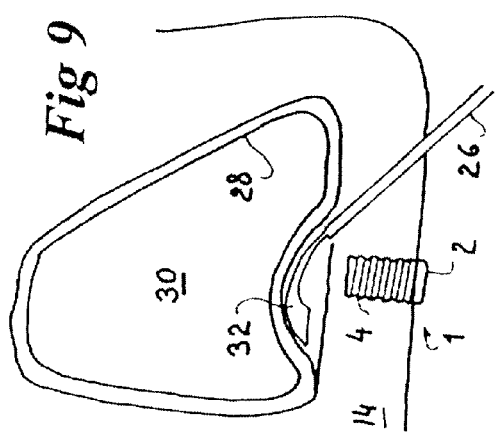
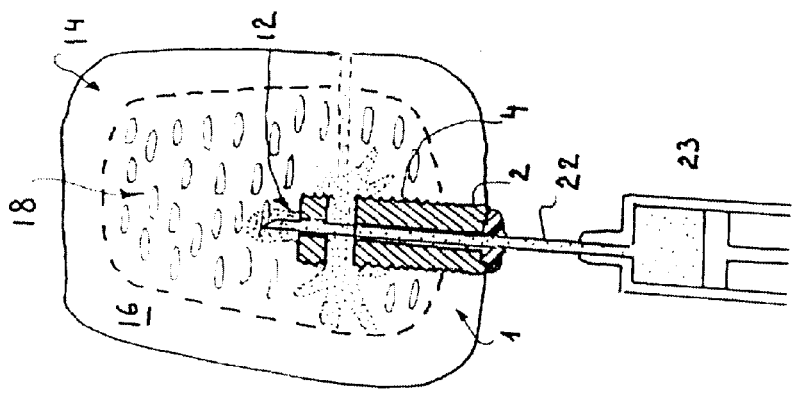

DENTAL IMPLANT

The invention concerns dental implants.

A dental implant is the prosthetic equivalent of the root of a tooth. Despite appearances, the root of a tooth, with its very small volume, is endowed with astonishing properties. It must be able to withstand stresses of the order of ten to thirty kg per $cm^2$, and its substance must be able to resist the mechanical stresses generated by mastication.

The root in fact serves to transmit the masticatory forces from the muscles to the crown of the tooth via the jaw bones. The contact between the bone seat and the root is thus of crucial importance. The problem is that a bone is not a homogeneous structure: beneath its very strong cortical walls extends its medullary zone, which is of spongy appearance and offers negligible mechanical support for an implant. It is therefore imperative that a dental implant passes through the medullary zone and anchors firmly in the cortical walls. Current dental implants thus require at least 8 to 15 mm of bone structure in order to be fitted in place. This fitting is done by screwing after a hole has been drilled in the upper or lower jaw bone.

However, this technique can only be used on patients who have a sufficient bone support, corresponding to classification SD 1 in implantology.

This classification is based on the height of the floor of the maxillary sinus in the technique of bicortical implants; SD1 corresponds to a floor height of greater than 10 mm.

According to the same classification, SD2 corresponds to a floor height of between 8 and 10 mm, SD3 to a floor height of between 5 and 8 mm, and SD4 to a floor height of between 0 and 5 mm (which requires filling).

In addition, after the implant support has been fitted in place, it is generally necessary to wait nearly five months before being able to place any load on the crown of the tooth.

EP 336,082 has disclosed a dental pin with a thread pitch used to fix a crown in the root of a tooth. Orifices are provided in the pin for the purpose of axial injection of a cement. However, such a technique cannot be applied to the jaw.

The alveolar bone has the role of supporting the teeth. When these disappear, the bone, which has lost its inherent function, is resorbed. The bone can also degrade for other reasons (various conditions, tumours, etc.).

For subjects corresponding to higher stages of deterioration (SD2, SD3 and SD4), the cortical parts of the bone support no longer provide a sufficient thickness for fitting an implant. In this case, a bone graft is performed in the maxillary sinus in order to increase the thickness of the bone support. The grafts used are slivers of bone taken from the patient himself. After ossification (which itself generally takes about 5 months), an implant can be fitted in place in accordance with the principles described above.

The object of the invention is to make it possible to treat stages SD2 or above without recourse to major treatment. Another object of the invention is to be able to permit immediate loading of the implanted tooth.

The subject of the invention is a dental implant for anchoring in a bone structure, comprising a head intended to support a dental prosthesis and a threaded root of cylindrical substance, in which the threaded root has an internal cavity and at least one lateral orifice connecting this internal cavity and the external lateral face of the root, the axial position of this orifice being such that when the implant is in position, this at least one orifice opens out on a medullary zone of the bone structure.

The dimensions of this at least one lateral orifice advantageously allow a hardenable material to be introduced into the internal cavity via a hollow needle.

The internal cavity can also have an axial orifice at its distal end.

This at least one lateral orifice preferably has an oval cross section, the main axis of this oval cross section extending in a plane perpendicular to the axis of the root.

The axial length is preferably between 3 and 8 mm.

According to an advantageous embodiment, the implant comprises a device for indicating the position of the lateral orifice, for example a removable tongue which can be attached to the head of the implant.

Another subject of the invention is a kit designed for fitting a dental implant in place, comprising:
- an implant such as has been described above;
- a biocompatible hardenable fluid;
- a device for indicating the position of the lateral orifice of the implant;
- a hollow needle injection device with which, when the implant is in place, it is possible to inject the biocompatible hardenable fluid through the bone and into the internal cavity of the implant;
- optionally, a spatula which is retractable in a hollow needle; the hollow needle is preferably made of a shape-memory metal, capable of changing from an initial straight shape to a curved shape.

Another subject of the invention is a method for fixing a dental implant in a jaw bone, which method comprises the following operations:
- drilling a hole in the jaw bone from its cortical wall as far as a medullary zone in such a way as to form an alveolus with the dimensions of an implant;
- screwing into place an implant whose threaded root has an internal cavity, at least one lateral orifice connecting this internal cavity and the external lateral face of the root, the axial position of this orifice being such that when the implant is in position, this at least one orifice opens out on a medullary zone of the bone structure;
- inserting a hollow needle through the jaw bone as far as the alveolus;
- injecting a biocompatible hardenable fluid into the internal cavity of the implant;
- distributing the hardenable fluid in the volume around the prosthesis, in the lateral orifices and in the internal cavity of the implant;
- partially withdrawing the hollow needle;
- distributing the hardenable fluid in the medullary zone of the jaw;
- leaving the hardenable fluid to harden.

This method can additionally comprise the following operations:
- inserting a hollow needle through the jaw bone to a point below the mucosa of the maxillary sinus, substantially level with the alveolus of the implant;
- deploying a spatula via the hollow needle;
- detaching the mucosa from the bone using the spatula;
- retracting the spatula through the hollow needle;
- injecting a biocompatible hardenable fluid between the bone and the mucosa.

Other particularities and advantages of the invention will become apparent from the following description of particular embodiments, reference being made to the drawings in which:

FIGS. 1 to 3 are perspective views of the implant of the invention;

FIGS. 4, 5 and 7 are diagrammatic perspective views of an implant of the invention during fitting;

FIG. 6 is a cross-sectional view on the plane VI—VI of the implant in FIG. 4;

FIGS. 8 and 9 are diagrammatic perspective views, with part cut away, of two stages of reinforcing the wall of the jaw for an implant of the invention;

FIGS. 10 and 11 are diagrammatic views of a head of a spatula with retractable blade according to the invention.

FIGS. 1 to 3 show three possible variants of the implant 1 of the invention.

This implant has a conventional head 2 intended to support a dental prosthesis and a threaded root 4 of cylindrical substance.

A series of longitudinal grooves 6 formed along the root allow the implant to tap the wall of the alveolus as it proceeds through the bone structure.

Near its distal part, the root 4 is provided with a lateral orifice 8 of substantially oval shape which opens into a cavity 10 of the root 4, the end of which is therefore hollow.

The lateral orifice 8 can open out at different positions of the root 4 (see FIGS. 1 and 2). The root 4 can be provided with an axial orifice 12 opening out towards its tip.

FIG. 4 shows the implant 1 after its introduction into a jaw bone 14. As will be seen, the root 4 passes through the hard cortical wall 16 of the bone and plunges into the spongy medullary zone 18 of the bone which contains the marrow. The position of the lateral orifice 8 on the root 4 is such that this orifice 8 opens into this medullary zone 18 of the bone 14.

FIG. 5 shows a subsequent phase of the fitting of the implant 1. A device 20 for indicating the angular position of the lateral orifice 8 (in this case a calibrated tongue) has been clipped onto the head 2 of the implant 1. The needle 22 of an injection device 23 has been introduced, perforating the bone of the jaw, as far as the opening 8 of the cavity 10 of the root 4. The presence of the indicator tongue 20 (in combination with medical imaging) renders the positioning extremely reliable. At this point, a biocompatible hardenable product 24 (cement, polymerizing or precipitating agent) is injected into the implant 1 via the needle. This injection is continued until the hardening product 24, emerging from the cavity 10, fills the volume around the prosthesis and the adjacent medullary alveoli. The expansion of the product 24 can be promoted by gradually withdrawing the needle while continuing the injection, as is shown in FIG. 5.

After the hardenable product 24 has set completely, the implant 1 is solidly implanted in the jaw bone 14 and can be loaded without delay.

FIG. 6 is a cross-sectional view of the implant 1. As is shown, the needle 22 can be a conventional straight needle. However, it is also possible to use a curved needle 25, or, better still, a needle with shape memory whose tip curves after its introduction. The benefit of a curved needle 25 is that of increasing the volume of injection of the hardenable fluid on both sides of the implant 1, as far as the controlateral margin of the cortical support of the bone, then, by withdrawing the needle 22, 25, as far as the ipsilateral margin at the point of entry of the needle 22, 25.

There is the possibility of injecting the biocompatible hardenable fluid through the lumen of the prosthetic hole which can communicate with the apex of the implant (see FIG. 7). This can be done via the head of the implant, via a prosthetic attachment placed on this head, or via a needle inserted through the implant. This technique is of interest as regards the mandible.

The advantages of the present implant over the conventional implants are multiple. This is because it is no longer necessary to wait several months before complete ossification of the zone around the prosthesis, which in fact considerably curtails the suffering of the patients and eliminates the many intermediate interventions prior to fitting the crowns on the implant.

In addition, the hardenable product 24 is gradually colonized by the organism and replaced by a solid bone seat.

Finally, the length of the implant is considerably reduced (3 to 8 millimetres, depending on the available height, as opposed to 8 to 15 mm for a conventional implant), which makes it possible to fit dental implants even in patients who cannot be operated on using conventional methods.

Moreover, if the thickness of the patient's jaw bone 14 is too small, it is nevertheless still possible to fit an implant 1 according to the invention by utilizing the volume of the maxillary sinuses.

With a conventional implant, this method would be applicable only by performing a very long preparatory intervention. The ossification of the grafts on the back of the jaw bone will take nearly 5 months until a cortical wall is obtained which is sufficiently hard and stable to allow an implant to be screwed in.

FIGS. 8 and 9 show how it is possible to strengthen the jaw during the fitting of an implant of the invention.

A needle 26 is introduced, with imaging control, through the jaw bone 14 to a point below the mucosa 28 of the maxillary sinus 30 in order to detach this mucosa 28. This detaching is done using a shape-memory spatula as described with reference to FIGS. 10 and 11. This needle 26 whose tip can be made of diamond or other material is hollow and contains a shape-memory mandrel 32 which, once it has emerged from the needle, deploys in order to form a spatula 26 allowing the mucosa to be detached. After the spatula 26 has been folded up again and the shape-memory mandrel 32 has been withdrawn, a cement 24 of the same composition as before can be injected through the needle 26 into the pocket formed between the detached mucosa 28 and the jaw bone 14, which makes it possible to recover the height and screw in a larger implant 1.

It will be noted that the mucosa 28 can be detached by injection of a liquid or gas or by manual detachment, or else by direct injection of the polymerizing or precipitating agent.

With the technique of implants immobilized by sealing, it is possible to imagine treating SA2, SA3, SA4, but also mandibular cases where osteoporosis has caused the disappearance of all traces of trabeculation at the medullary level. This technique permits primary immobilization (from the first surgical intervention) of the implant without having bicortical blocking, and hence immediate loading of the implant.

What is claimed is:

1. A kit designed for fitting a dental implant in place, comprising:

a dental implant for anchoring in a bone structure, comprising a head intended to support a dental prosthesis and a threaded root of cylindrical substance, wherein the threaded root has an internal cavity and at least one lateral orifice through which said internal cavity opens out on the external lateral face of the root, the axial position of said orifice being such that when the implant is in position, said at least one orifice opens out on a medullary zone of the bone structure;

a biocompatible hardenable fluid;

a device for indicating the position of the lateral orifice of the implant;

a hollow needle injection device for injecting the biocompatible hardenable fluid through the bone and into the internal cavity of the implant when the implant is in place; and a spatula which is retractable in the hollow needle.

2. A kit designed for fitting a dental implant in place according to claim 1, wherein the hollow needle is made of a shape-memory metal, capable of changing from an initial straight shape to a curved shape.

3. Method for fixing a dental implant in a jaw bone, which method comprises the following operations:

drilling a hole in the jaw bone from its cortical wall as far as a medullary zone in such a way as to form an alveolus with the dimensions of an implant;

screwing into place an implant whose threaded root has an internal cavity, at least one lateral orifice connecting this internal cavity and the external lateral face of the root, the axial position of this orifice being such that when the implant is in position, this at least one orifice opens out on a medullary zone of the bone structure;

inserting a hollow needle through the jaw bone as far as the alveolus;

injecting a biocompatible hardenable fluid into the internal cavity of the implant;

distributing the hardenable fluid in the volume around the prosthesis, in the lateral orifices and in the internal cavity of the implant;

partially withdrawing the hollow needle;

distributing the hardenable fluid in the medullary zone of the jaw;

leaving the hardenable fluid to harden.

4. Method as claimed in claim 3, wherein the method comprises the following operations:

inserting a hollow needle through the jaw bone to a point below the mucosa of the maxillary sinus, substantially level with the alveolus of the implant;

deploying a spatula via the hollow needle;

detaching the mucosa from the bone using the spatula.

5. Method as claimed in claims 3 or 4 wherein a hollow needle is used made of a shape-memory metal, capable of changing from an initial straight shape to a curved shape.

6. A method for fixing a dental implant in a jaw bone, said method comprising:

drilling a hole in a jaw bone from the cortical wall as far as a medullary zone in such a way as to form an alveolus with the dimensions of an implant;

screwing into place an implant, said implant having a threaded root with an internal cavity, at least one lateral orifice connecting the internal cavity and an external lateral face of the root, the axial position of the at least one orifice being such that when the implant is in position, the at least one orifice opens out on a medullary zone of the bone structure;

inserting a hollow needle through the jaw bone as far as the alveolus;

injecting a biocompatible hardenable fluid into the internal cavity of the implant so as to distribute the hardenable fluid in the volume around the implant, in the at least one lateral orifice and in the internal cavity of the implant, partially withdrawing the hollow needle;

distributing the hardenable fluid in the medullary zone of the jaw; and allowing the hardenable fluid to harden.

7. The method of claim 6, further comprising:

inserting a second hollow needle through the jaw bone to a point below the mucosa of the maxillary sinus, substantially level with the alveolus of the implant;

deploying a spatula via the second hollow needle; and detaching a portion of the mucosa from the bone using the spatula.

\* \* \* \* \*